(12) United States Patent
Zhang

(10) Patent No.: US 9,933,418 B2
(45) Date of Patent: Apr. 3, 2018

(54) MULTI-UNIT PLATE FOR ELECTROBLOTTING AND IMMUNOBLOT ANALYSIS

(71) Applicant: Jiandi Zhang, Fairfax, VA (US)

(72) Inventor: Jiandi Zhang, Fairfax, VA (US)

(73) Assignee: QUANTICISION DIAGNOSTICS INC., Chapel Hill, NC (US)

( * ) Notice: Subject to any disclaimer, the term of this patent is extended or adjusted under 35 U.S.C. 154(b) by 0 days.

(21) Appl. No.: 14/721,205

(22) Filed: May 26, 2015

(65) Prior Publication Data

US 2016/0349244 A1    Dec. 1, 2016

(51) Int. Cl.
*C12Q 1/68* (2018.01)
*G01N 33/53* (2006.01)
*B01L 3/00* (2006.01)

(52) U.S. Cl.
CPC ........ *G01N 33/5304* (2013.01); *B01L 3/5085* (2013.01); *B01L 2300/0609* (2013.01); *B01L 2300/069* (2013.01); *B01L 2300/0829* (2013.01); *B01L 2300/163* (2013.01)

(58) Field of Classification Search
CPC ........... B01L 3/5085; B01L 2300/0829; B01L 3/50255

USPC .................................................. 422/553, 552
See application file for complete search history.

(56) References Cited

U.S. PATENT DOCUMENTS

| | | | | |
|---|---|---|---|---|
| 5,062,308 A | * | 11/1991 | Rising | B01D 29/01 |
| | | | | 73/864.41 |
| 5,650,323 A | * | 7/1997 | Root | B01L 3/5085 |
| | | | | 210/238 |
| 6,309,605 B1 | * | 10/2001 | Zermani | B01L 3/5025 |
| | | | | 210/451 |
| 2005/0103703 A1 | * | 5/2005 | Young | B01L 3/50255 |
| | | | | 210/450 |
| 2007/0003448 A1 | * | 1/2007 | Kanigan | B01L 3/5025 |
| | | | | 422/400 |
| 2010/0190197 A1 | * | 7/2010 | Martin | B01L 3/50255 |
| | | | | 435/29 |

* cited by examiner

*Primary Examiner* — Jyoti Nagpaul
(74) *Attorney, Agent, or Firm* — Novick, Kim & Lee, PLLC; Allen Xue

(57) ABSTRACT

This invention is provided for multi-unit plate with at least one unit comprised of a membrane, preferably nitrocellulose or PVDF membrane, associated with a supporting structure to allow for electroblotting of the membrane. This multi-unit plate is suited for high throughput immunoblot analysis including Zestern analysis.

11 Claims, 2 Drawing Sheets

1A

1B

1C

1D

1I

1J

1K

MULTI-UNIT PLATE FOR ELECTROBLOTTING AND IMMUNOBLOT ANALYSIS

FIELD OF INVENTION

The present invention relates to the field of immunoblot analysis and more particularly, to device and method for high throughput immunoblot analysis. In one application, the present invention is of multi-unit plate and method for performing Zestern analysis in a multi-unit format.

BACKGROUND ART

Protein analysis is the foundation of modern biological research. Investigations of the expression and regulation of critical protein factors in biological processes and their applications in pharmaceutical and clinical studies provide vital information for experimental, pharmaceutical and clinical research of the pathogenesis of diseases and their prevention, diagnosis and treatments.

The recently patented Zestern technique (U.S. Pat. Nos. 8,293,487, 8,563,256 and 8,722,345) is an improvement of traditional methods of immunoblot-based protein analysis. While the protein samples are analyzed following a traditional immunoblotting process before detection, an additional step of elution is added in Zestern analysis to ensure the specificity of the assay. The antibody or antibody complex bound to the antigen of interest can be specifically competed out by competing molecule into elution solution. The amount of the eluted antibody or antibody complex in elution solution reflect the amount of antigen of interest in the sample to be analyzed. The total amount of eluted antibody or antibody complex can be quantified directly in solution, representing another advantage of Zestern analysis over traditional immunoblotting methods.

While Zestern analysis demonstrates advantage over traditional immunoblot methods for its simplicity and suitability for high throughput analysis, it poses new demand for suitable devices, as current existing devices for traditional immunoblot methods are not designed to meet the need of Zestern analysis, especially for high throughput purpose.

In traditional immunoblot analysis, represented by Western blot analysis, several types of membranes have been used and well optimized for immunoblot analysis. These membranes include both nitrocellulose membrane and PVDF membrane.

In traditional immunoblot analysis, the signal is detected on the very spot where the antibody or antibody complex bound to the antigen of interest on the membrane. This requires the membrane to be smooth and continuous to facilitate comparison of the detection results.

On the contrary, in Zestern analysis, antibody or antibody complex is liberated from the very spot where antibody or antibody complex bound to the antigen of interest by the competing molecule. The antibody or antibody complex is eluted from each spot respectively for quantification. Clearly, in Zestern analysis, the membrane cannot be continuous among protein samples. It must be separated from each other to allow elution of antibody or antibody complex for each protein sample separately, preventing cross-contamination of the signal from each other.

In Zestern analysis, for the membrane per se, there is no requirement regarding the shape or other physical characteristics of the membrane, as detection of the signal from each sample is not being processed on the membrane per se.

Multi-well plate has been widely used in biochemical assays and immunoblotting assays including ELISA assays. These multi-well plates include 6, 24, 96, and even 1536 well plate. It can also be referred as microtiter plate, microplate, or microwell plate.

Multi-well plate for ELISA assay generally has protein binding capacity at less than 1 $\mu g/cm^2$. In contrast, a typical membrane for traditional immunoblotting, regardless of nitrocellulose or PVDF membrane, has protein binding capacity of 100 to 200 $\mu g/cm^2$. While ELISA plate has achieved success in ELISA assay, its low protein binding capacity limits its application in Zestern analysis.

In the prototype of immunoblot analysis, Dot blot analysis, the antigen is applied directly to the membrane, and the membrane is allowed to dry in the air over an extended period of time. This practice may not to be the best form of sample application, for at least in routine practices, vacuum is applied to the membrane to increase the binding of the antigen to the membrane.

In Western blot analysis, antigen is trapped in the polyacrylamide gel during electrophoresis step. The trapped antigen is transferred to the membrane for blotting through a process called electroblotting.

In this invention, a multi-unit plate is designed both suitable for Zestern analysis and for electroblotting of the antigen to the membrane. Therefore, this invention provides solution to the unique demand of Zestern analysis for immunoblot analysis, especially for its application in multi-unit plate format. It also significantly increase the amount of antigen bound to the membrane due to electroblotting step.

SUMMARY OF THE INVENTION

The reference to the "present invention" or "invention" used herein relates to exemplary embodiments and not necessarily to every embodiment that is encompassed by the appended claims.

The present invention provides method and device and variations of the device for high throughput immunoblot analysis including Zestern analysis. While the devices may be different from each other, at least one unit within the multi-unit plate is comprised of a membrane associated with supporting structure for immunoblotting and electroblotting of protein sample in immunoblot analysis.

The supporting structure can be in any shape, as long as it serves the purpose to separate membrane of individual unit from each other within the multi-unit plate.

In Zestern analysis, membrane used for individual sample may be a piece of membrane, or pieces of membrane together in a unit of the multi-unit plate. The membrane is eluted in the elution step for quantification of the individual sample.

There is no limitation of the shape, texture or even the continuation of the membrane within the individual unit of multi-unit plate. Multiple pieces of membrane can be considered as one membrane as long as they are within one unit of multi-unit plate.

One method of Zestern analysis is to use multi-unit plate with at least one unit comprised of a membrane and supporting structure to allow immunoblot analysis and electroblotting. The membrane can associate with the supporting structure in any form, as long as the membrane of one unit is separated from other unit within the multi-unit plate, and it allows the electroblotting process to happen.

One example of supporting structure is a hollow protrusion with opening on both ends as individual unit of multi-unit plate, and membrane is associated with the protrusion.

The membrane can be at any position within the hollow protrusion. It may be in the middle inside the protrusion or at either ends of the hollow protrusion, including covering either end of the hollow protrusion.

The hollow protrusion may have opening on the sidewall of the unit to allow efficient washing of the membrane. It may have more than one opening on the sidewall of the unit. In one embodiment of the present invention, a whole section of the hollow structure in-between may be missing, and the separated sections of the hollow structure are connected by a pole-like structure. In another embodiment of the invention, the hollow protrusion may become a ring shape structure with a pole-like structure attached alongside to form the multi-unit plate. The membrane is associated with the ring structure.

In one embodiment of the invention, the rim where the supporting structure is in direct contact with the membrane is closed. In another embodiment of the invention, that rim is open. The preferred shape of the rim is circular. However, other shapes are acceptable as long as the multi-unit plate can fit into a multi-well plate.

The present invention may be combined with one conventional multi-well plate to complete Zestern analysis. The wall of individual well of the multi-well plate serves as physical barrier to prevent cross contamination of elution solution from each other.

The multi-unit plate is processed in a typical immunoblot process until at the elution step of the Zestern analysis, where it combines with a multi-well plate to allow for elution of antibodies from individual unit of multi-unit plate.

The multi-unit plate, until the elution step, can be processed individually, or it can be processed as a group. Nonetheless, at the elution step, the multi-unit plate needs to be used individually with a matching multi-well plate.

Preferably, the plurality of units of a plate of the present invention comprise 6n units arranged in a 2n by 3n array, where n is an integer greater than 0, the units preferably being arranged in rectangular packing. Preferred pluralities of units are the commonly known pluralities of units such as 6, 24, 96, 384 and 1536 units. More preferred are plates of 96 units and 384 units as these formats are most popular and have many available accessories including fluid handling accessories such as fluid-handling robots.

In one embodiment of the present invention, the individual unit in multi-unit plate can be individually addressable.

A multi-unit plate of the present invention is made of membrane and any suitable, non-electrically conductive material. Suitable materials include but are not limited to ceramics, elastomers, epoxies, glasses, glass-ceramics, plastics, polycarbonates, polydimethlsiloxane, polyurethane, polyethylenterephatalate glycol, polymers, polymethyl methacrylate, polystyrene, polyvinyl chloride, rubber, silicon, silicon oxide and silicon rubber.

There is no limitation of the shape or 3-dimensional structure of the membrane used in multi-unit plate as long as it allows accessibility of the samples of interest. In an embodiment of the present invention, the surface of the membrane in one unit of multi-unit plate may be smooth. In another embodiment of the present invention, the surface of individual membrane may not be smooth.

In an embodiment of the present invention, the individual membrane may be treated before or after sample application to increase protein binding efficiency.

In an embodiment of the present invention, the multi-unit plate in combination with a multi-well plate can be used to analyze samples in traditional immunoblot analyses. A sample of interest is applied to membrane of an individual unit of the multi-unit plate of present invention, and the membrane is going through electroblotting, washing, antibody incubation, and washing steps before it is placed in a conventional multi-well plate for direct detection using a microplate reader and appropriate reagents.

Additional aspects of the invention will be set forth, in part, in the detailed description, figures, and any claims which follow, or can be learned by practice of the invention. It is to be understood that both the foregoing general description and the following detailed description are exemplary and explanatory only, and are not restrictive of the invention as disclosed.

DETAILED DESCRIPTION OF THE INVENTION

Figure 1:
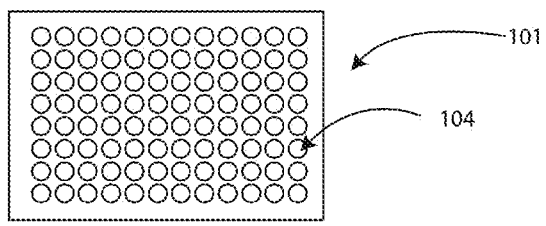
FIG. 1 shows an embodiment of multi-unit plate. 1A, top view of the multi-unit plate; 1B, side view of the multi-unit plate; 1C, cross-section view of the multi-unit plate; 1D, structure of an individual unit of multi-unit plate; including both the side view and cross-section view of an individual unit; 1E-1H, Several embodiments of individual unit of multi-unit plate; 1I-1J, embodiments of rim of supporting structure in direct contact with membrane; 1K, side view of individual unit with rim shown in FIG. 1J. 101, multi-unit plate of present invention; 102, overall supporting structure of multi-unit plate; 103, membrane associated with the overall supporting structure of multi-unit plate; 104, An individual unit of multi-unit plate include both the supporting structure of individual unit and membrane; 105, supporting structure of an individual unit; 106; membrane associated with supporting structure of an individual unit; 107, A closed rim of the supporting structure of an individual unit in contact with membrane; 108, An open rim of supporting structure of an individual unit in contact with membrane; 109, pole like structure to link two sections of the hollow structure together; 110, opening on the sidewall of an individual unit of multi-unit plate.
Figure 1:
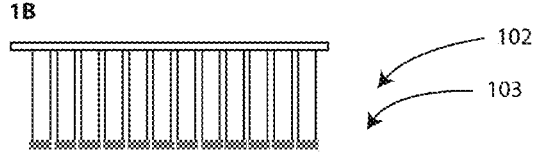
Figure 1:
Figure 1:
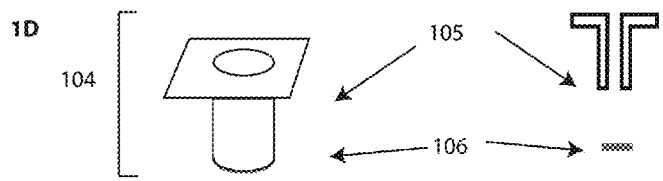
Figure 1:
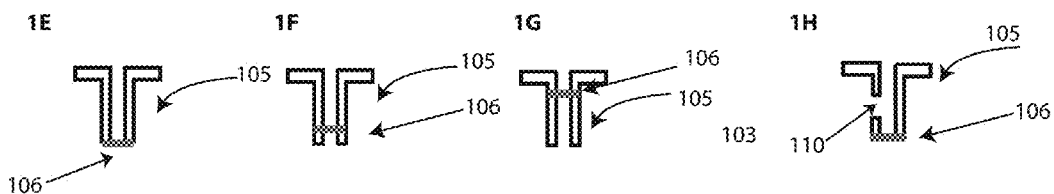
Figure 1:
Figure 1:
Figure 1:
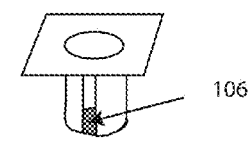

Unless defined otherwise, all technical and scientific terms used herein have the same meaning as is commonly understood by one of skills in the art to which this invention belongs.

The present invention provides devices for immunoblot analysis including Zestern analysis. Zestern analysis distinguishes itself from traditional immunoblot analysis including Western blot analysis by its simplicity and suitability for multi-unit format. The elution step in Zestern analysis requires elution solution for individual sample to be physically separated from each other to avoid cross-contamination of the result. In other word, each sample must be applied to individual membrane, and elution solution for individual sample must be limited to membrane within individual unit of multi-unit plate.

In an embodiment of present invention, device for Zestern analysis is shown in the drawing. A multi-unit plate 101 includes overall supporting structure 102 and membrane 103. Membrane 103 is preferably either PVDF or nitrocellulose membrane.

Individual unit 104 includes both the supporting structure 105 and membrane 106. The supporting structure 105 is hollow inside, with opening on both ends. Sample to be analyzed is applied directly on the membrane 106 within an individual unit 104.

In one embodiment of the present invention, membrane 106 is at the bottom of the hollow supporting structure 105 of an individual unit of 104 as in FIG. 1E. In yet another embodiment of present invention, it is in the middle within the hollow supporting structure 105 of an individual unit of 104 as in FIG. 1F. In yet another embodiment of the invention, it is at the top part of the hollow supporting structure 105 of an individual unit 104. In one embodiment of present invention, there may have an opening 110 on the sidewall of hollow supporting structure 105 of an individual unit 104. In yet another embodiment of present invention, there may be more than one opening 110 on the sidewall of the supporting structure of an individual unit 104.

In one embodiment of the present invention, the rim 107 of the supporting structure of an individual unit in direct contact with membrane 106 is closed, as shown in FIG. 1I. In yet another embodiment of the present invention, the rim 108 of the supporting structure of an individual unit in direct contact with membrane 106 is open, as shown in FIGS. 1J and 1K.

Figure 2:
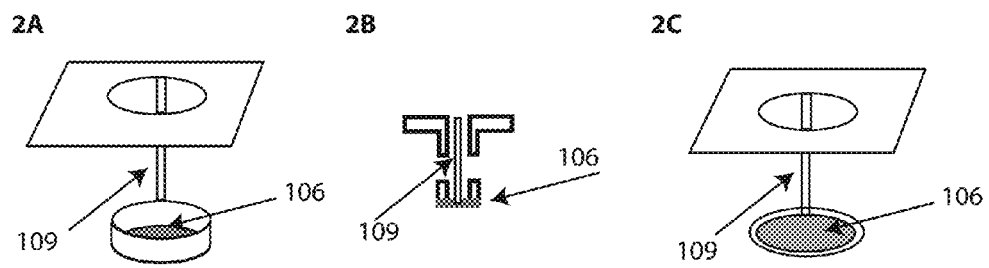
FIG. 2 show several other embodiments of individual unit of multi-unit plate; 2A, Front view of an individual unit; 2B, side view of an individual unit; 2C, another embodiment of an individual unit of multi-unit plate.

In another embodiment of present invention, the whole section between the upper and lower parts of the sidewall of the hollow supporting structure 105 is missing, and the upper and lower parts of supporting structure are connected by a pole-like structure 109 in-between. In yet another embodiment of present invention, a membrane is attached to a ring shape structure, and this ring shape structure is connected to the multi-unit plate by a pole like structure 109, as shown in FIG. 2C.

Preferably, a plate of the present invention has a footprint of a standard multi-well plate, so the multi-unit plate can fit inside a typical multi-well plate. Preferably, the plurality of units of a plate of the present invention comprise 6n units arranged in a 2n by 3n array, where n is an integer greater than 0, the units preferably being arranged in rectangular packing. Preferred pluralities of units are the commonly known pluralities of units such as 6, 24, 96, 384 and 1536 units. More preferred are plates of 96 units and 384 units as these formats are most popular and have many available accessories including fluid handling accessories such as fluid-handling robots.

The surface of the membrane 103 can be smooth, or it can be coarse. It can also have protrusions on the surface of the membrane.

The antigen is applied directly on the membrane of at least one unit of multi-unit plate for electroblotting. Those skilled in the art will know that membrane is permeable to allow the electroblotting process. Those skilled in the art will know that while the pore of the membrane may vary, it must restrict the free passage of antigen of interest through the membrane.

The supporting structure 102 of multi-unit plate is made of any suitable, non-electrically conductive material. Suitable materials include but are not limited to ceramics, elastomers, epoxies, glasses, glass-ceramics, plastics, polycarbonates, polydimethylsiloxane, polyurethane, polyethylenerephatalate glycol, polymers, polymethyl methacrylate, polystyrene, polyvinyl chloride, rubber, silicon, silicon oxide and silicon rubber.

The multi-unit plate 101 with immunocomplex bound on the membrane 106 of individual unit of plate 104 is inserted into a typical multi-well plate after a typical immunoblotting process. Elution solution containing competing molecule is applied in individual well of multi-well plate to elute antibody or antibody complex from membrane 106 for quantification of the signals.

The membrane 106 of the individual unit of 104 is made of any suitable material with protein binding capacity comparable to nitrocellulose or PVDF membrane. The entire plate of the present invention can be made of one material, or it can be made of a number of different materials, for example, a plurality of layers.

As used herein "membrane" is to be taken in its broadest context. A membrane can be any material with sufficient surface porosity to allow access by detection antibodies and a suitable surface affinity to bind antigen. All these materials may be used in suitable shapes, or they can be coated onto, or bonded or laminated, or simply attached to appropriate supporting material, such as paper, glass, plastic materials, as long as it may not interfere with the electroblotting process. For example, membrane can be, but not limited to, nitrocellulose membrane or PVDF membrane.

Those skilled in the art will know how to prepare samples for immunoblot purpose. The samples include, but not limited to, a mixture of a chemical molecule, a peptide molecule, a protein molecule, an RNA molecule, a DNA molecule, a traditional antibody, e.g, two heavy chains and two light chains, a recombinant antibody or fragment, a cell, a virus particle, and a product comprising crosslinking any two or more of the above. The sample may be charged with appropriate sample buffer.

Those skilled in the art will know how to treat membrane for immunoblot analysis. These practices include, but not limited to, direct application of a sample to the membrane, or pre-wet the membrane with Ethanol, or Methanol, before sample application. The multi-unit plate with samples applied on the membrane may be left in the air to dry before going through a typical immunoblot process including electroblotting.

Those skilled in the art know how to prepare membrane for electroblotting. The membrane applied with sample is placed inside the transfer buffer under appropriate current to increase the amount of proteins bound onto the membrane.

As used herein "the conventional multi-well plate" is to be taken in its broadest context. The conventional multi-well plate can be any plate the multi-unit plate of present invention can fit inside to physically separate individual unit of multi-unit plate from each other.

Those skilled in the art will know how to process an individual membrane with a sample applied on the surface for immunoblot process. These steps include blocking the individual membranes with blocking buffer, incubation with primary antibody, washing, incubation with secondary antibody and washing again to eliminate non-specific antibody bound to the membrane.

In yet another embodiment of present invention, the multi-unit plate of present invention can be used for traditional immunoblot analysis including ELISA analysis, Dot blot analysis, in cell western analysis and protein array analysis. The significantly increased binding capacity of the membrane, in combination with the significantly increased binding efficiency due to electroblotting, are suitable for high throughput immunoblot analysis.

A protein sample is applied to the membrane of an individual unit of multi-unit plate of present invention. The membrane is going through electroblotting and a series of typical immunoblot steps including blocking, primary antibody incubation, washing, secondary antibody incubation, and washing steps before it is placed in a conventional multi-well plate. The amount of antibodies bound on the membrane in individual unit of multi-unit plate of present invention can be detected using microplate reader by adding appropriate detection reagents to the individual well of multi-well plate containing the multi-unit plate of present invention, and the signal can be detected either directly in the individual well of multi-well plate containing the multi-unit plate of present invention, or the solution can be transferred from individual well of multi-well plate containing multi-unit plate of present invention into another multi-well plate for quantification using a microplate reader.

Although several embodiments of the present invention have been illustrated in the accompanying Drawings and described in the foregoing detailed description, it should be understood that the invention is not limited to the embodiments disclosed. It is appreciated that many alternatives, modifications and variations will be apparent to those skilled in the art. Accordingly, the present invention is intended to embrace all such alternatives, modifications and variations that fall within the spirit and broad scope of the appended claims.

The following examples of the method of invention are to further illustrate of the nature of the invention. It needs to be understood that the invention is not limited thereto.

Example 1

Samples of interest are prepared using 4×SDS buffer (Laemmli buffer). The 96 unit plate of present invention is loaded with 6 μl of whole cell lysate of HEK-293 cells.

The multi-unit plate is subjected to electroblotting for 20 mins.

A typical immunoblot process, including steps of blocking, incubation with primary antibody, washing, incubation with secondary antibody, and washing, is performed using present invention of multi-unit plate. The secondary antibody is labeled with Horseradish peroxidase as the reporter enzyme for immunoblot analysis.

The multi-unit plate is placed into a multi-well plate containing elution buffer of competing molecule or TBS at 100 μl/well for 15 mins to liberate antibody complex from the membrane of multi-unit plate.

The elution buffer is transferred to a regular 96 well plate for quantification of the signaling using a typical chemiluminescence reporter assay kit (Millipore) with a microplate reader.

Example 2

Samples of interest are prepared using 4×SDS buffer (Laemmli buffer). The 96 unit plate of present invention is loaded with 6 μl of whole cell lysate of HEK-293 cells.

The multi-unit plate is subjected to electroblotting for 20 mins.

A typical immunoblot process, including steps of blocking, incubation with primary antibody, washing, incubation with secondary antibody, and washing, is performed using multi-unit plate of present invention. The secondary antibody is labeled with Horseradish peroxidase as the reporter enzyme for immunoblot analysis.

The multi-unit plate is placed into a multi-well plate. TBS of 40 μl is mixed with prepared ECL solution (Millipore) at 1:1 ratio, and is added to the individual well of the multi-well plate holding the multi-unit plate of present invention.

After 10 mins, the ECL solution is transferred from the above-mentioned multi-well plate to a new multi-well plate at 60 μl/well for quantification using a microplate reader.

I claim:

1. A multi-unit plate for immunoblot analysis, comprising:
    a plate having a plurality of openings; and
    a plurality of protrusive members protruding away from the plate,
    wherein one or more of the plurality of protrusive members comprises an elongated linking member having a first end attached to the plate and a second end that provides a support structure having a membrane affixed to the support structure,
    wherein the support structure comprises a hollow center portion and a rim surrounding the hollow center portion, and
    wherein the membrane is affixed to the rim of the support structure.

2. The multi-unit plate of claim 1, wherein the elongated linking member is a rod and the rim in the support structure is a ring surrounding the hollow center portion and the membrane is affixed to the ring.

3. The multi-unit plate of claim 2, wherein the membrane is affixed to the side of ring disposed away from the plate.

4. The multi-unit plate of claim 1, wherein the elongated linking member is a tubular member having the first end attached to the plate and the second end having the rim, wherein the rim has one or more openings therein so that the membrane is separated from the tubular member at a hollow center portion of the tubular member and at the one or more openings in the rim of the second end of the tubular member.

5. The multi-unit plate of claim 1, wherein the membrane is a nitrocellulose or PVDF membrane.

6. The multi-unit plate of claim 1, wherein the support structure is made from a material selected from the group consisting of ceramics, elastomers, epoxies, glasses, glass-ceramics, plastics, polycarbonates, polydimethylsiloxane, polyethylenterephatalate glycol, polymers, polymethyl methacrylate, polystyrene, polyurethane, polyvinyl chloride, rubber, silicon, silicon oxide, and silicon rubber.

7. The multi-unit plate of claim 1, wherein the protrusive member comprises more than one elongated linking members.

8. The multi-unit plate of claim 1, wherein a number of the protrusive member is 6, 24, 96, 384, or 1536.

9. A method for immunoblot analysis, comprises:
    loading a sample containing a protein into one or more protrusive members of the multi-unit plate of claim 1;
    inserting the multi-unit plate into a multi-well plate so that each protrusive member of the multi-unit plate is placed inside a well of the multi-well plate;
    subjecting the membrane in one or more of the plurality of protrusive members successively to blocking with a blocking buffer, incubation with a primary antibody, washing, incubation with a secondary antibody, and washing to obtain one or more processed membranes;
    applying a detection reagent to the one or more processed membranes; and
    placing the multi-unit plate in a microplate reader.

10. The method of claim 9, wherein the sample is selected from the group consisting of a chemical molecule, a peptide molecule, a protein molecule, an RNA molecule, a DNA molecule, a traditional antibody, a recombinant antibody or fragment thereof, a cell, a virus particle, or mixtures thereof.

11. A device for immunoblot analysis, comprises a multi-unit plate of claim 1 and a multi-well plate, wherein the multi-well plate comprises a plurality of wells that receive the plurality of protrusive members of the multi-unit plate.

* * * * *